(12) United States Patent
Hajduch et al.

(10) Patent No.: US 7,858,606 B2
(45) Date of Patent: Dec. 28, 2010

(54) TRITERPENOID DERIVATIVES

(75) Inventors: Marian Hajduch, Olomouc (CZ); Jan Sarek, Ostrava-Poruba (CZ)

(73) Assignees: Univerzita Palackeho v Olomouci, Olomouc (CZ); Univerzita Karlova V Praze, Prague (CZ)

( * ) Notice: Subject to any disclaimer, the term of this patent is extended or adjusted under 35 U.S.C. 154(b) by 787 days.

(21) Appl. No.: 10/296,542

(22) PCT Filed: May 23, 2001

(86) PCT No.: PCT/GB01/02309

§ 371 (c)(1),
(2), (4) Date: Sep. 10, 2003

(87) PCT Pub. No.: WO01/90046

PCT Pub. Date: Nov. 29, 2001

(65) Prior Publication Data

US 2004/0087560 A1    May 6, 2004

(51) Int. Cl.
*A61K 31/56* (2006.01)
*C07J 53/00* (2006.01)
(52) U.S. Cl. .................. 514/177; 514/178; 514/179; 514/180; 514/181; 514/182; 552/510
(58) Field of Classification Search .................. 552/510
See application file for complete search history.

(56) References Cited

U.S. PATENT DOCUMENTS

| | | | |
|---|---|---|---|
| 6,221,873 B1 | 4/2001 | Havlicek et al. |
| 6,242,201 B1 | 6/2001 | Lane et al. |
| 6,472,507 B1 | 10/2002 | Fischer et al. |
| 6,531,479 B2 | 3/2003 | Wang |
| 6,569,833 B1 | 5/2003 | Fahraeus |
| 6,613,878 B1 | 9/2003 | Cox et al. |
| 6,699,854 B2 | 3/2004 | Wang |
| 6,703,395 B2 | 3/2004 | Havlicek |
| 6,943,026 B1 | 9/2005 | Balmain et al. |
| 6,962,792 B1 | 11/2005 | Ball |
| 6,992,169 B2 | 1/2006 | Fischer et al. |
| 7,041,701 B2 | 5/2006 | Hajduch et al. |
| 7,101,967 B2 | 9/2006 | Fischer et al. |
| 7,153,931 B1 | 12/2006 | Fischer et al. |
| 7,223,795 B2 | 5/2007 | Walkinshaw et al. |
| 7,262,202 B2 | 8/2007 | Fischer et al. |
| 2003/0036628 A1 | 2/2003 | Zheleva et al. |
| 2003/0152945 A1 | 8/2003 | Deak et al. |
| 2003/0170655 A1 | 9/2003 | Glover et al. |
| 2003/0229105 A1 | 12/2003 | Kashanchi |
| 2004/0029791 A1 | 2/2004 | Fahraeus et al. |
| 2004/0259894 A1 | 12/2004 | Wang et al. |
| 2005/0009846 A1 | 1/2005 | Fischer et al. |
| 2005/0153894 A1 | 7/2005 | Zheleva et al. |
| 2005/0153991 A1 | 7/2005 | Gianella-Borradori et al. |
| 2005/0159484 A1 | 7/2005 | Fischer et al. |
| 2005/0164976 A1 | 7/2005 | Green et al. |
| 2005/0192300 A1 | 9/2005 | Wang et al. |
| 2005/0215548 A1 | 9/2005 | Wang et al. |
| 2005/0222054 A1 | 10/2005 | Sleigh et al. |
| 2005/0256142 A1 | 11/2005 | Fischer et al. |
| 2005/0260730 A1 | 11/2005 | Fischer |
| 2005/0261260 A1 | 11/2005 | Gianella-Borradori |
| 2005/0267066 A1 | 12/2005 | Gianella-Borradori |
| 2005/0276866 A1 | 12/2005 | Gianella-Borradori |
| 2005/0277656 A1 | 12/2005 | Gianella-Borradori |
| 2005/0282843 A1 | 12/2005 | Wang et al. |
| 2005/0288307 A1 | 12/2005 | Wang et al. |
| 2006/0035909 A1 | 2/2006 | Fuksova et al. |
| 2006/0040997 A1 | 2/2006 | McInnes et al. |
| 2006/0148828 A1 | 7/2006 | Gianella-Borradori et al. |
| 2006/0160890 A1 | 7/2006 | Hajduch et al. |
| 2006/0183760 A1 | 8/2006 | Fischer et al. |
| 2006/0199830 A1 | 9/2006 | Wang et al. |
| 2006/0241297 A1 | 10/2006 | Wang et al. |

(Continued)

FOREIGN PATENT DOCUMENTS

EP     943620 A2     9/1999

(Continued)

OTHER PUBLICATIONS

Baddeley et al., "The oxidation of methyl acetylbetulate and methyl acetylmelaleucate by mercuric acetate.", Aust. J. Chem. vol. 24, pp. 2639-2648, 1971.*

(Continued)

*Primary Examiner*—Barbara P Badio
(74) *Attorney, Agent, or Firm*—Nelson Mullins Riley & Scarborough LLP; Cynthia L. Kanik; Brian C. Trinque

(57) ABSTRACT

The present invention relates to the use of a compound of formula (I), or a pharmaceutically acceptable salt, crystal form, complex, hydrate, or hydrolysable ester thereof, in the preparation of a medicament for treating a patient suffering from leukaemia, cancer or other proliferative disorder. A further embodiment relates to the use a compound of formula (I) in an assay for detecting the phosphorylation state of cellular substrates. The present invention also relates to novel compounds of formula (I), and the chemical synthesis thereof.

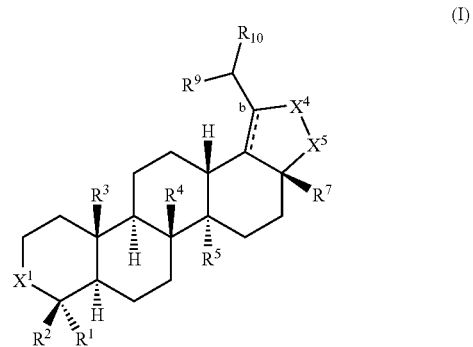

(I)

4 Claims, No Drawings

U.S. PATENT DOCUMENTS

| | | |
|---|---|---|
| 2006/0264628 A1 | 11/2006 | McInnes et al. |
| 2006/0281687 A1 | 12/2006 | Andrews et al. |
| 2006/0293245 A1 | 12/2006 | Zheleva et al. |
| 2007/0021419 A1 | 1/2007 | Wang et al. |
| 2007/0021452 A1 | 1/2007 | Wang et al. |
| 2007/0185134 A1 | 8/2007 | Fischer et al. |
| 2007/0270442 A1 | 11/2007 | Green et al. |

FOREIGN PATENT DOCUMENTS

| | | |
|---|---|---|
| GB | 1415601 | 11/1975 |
| WO | WO 98/51294 A2 | 11/1998 |
| WO | WO 00/24762 A1 | 5/2000 |

OTHER PUBLICATIONS

Klinotova et al., "Reaction of 18beta,19beta-epoxylupan-21-one derivatives with acids: A way to 21, 22-disubstituted lup-18-ene triterpenoids." Collect. Czech. Chem. Commun, 64(2), pp. 329-347, 1999.*

Dinda et al. "Reactions on naturally occurring triterpene: Part 1." *Indian J. Chem.* 1995; Sect B 34:624-628.

Kim et al. "Synthesis of betulinic acid derivatives with activity against human melanoma." *Bioorg. Med. Chem. Lett.* Jul. 7, 1998;8(13):1707-12.

Klinotová et al. "Reaction of 18β,19β-epoxylupan-21-one derivatives with acids: A way to 21,22-disubstituted lup-18-ene triterpenoids." *Collect. Czech. Chem. Commun.* 1999;64:329-347.

Konoshima et al. "Studies on inhibitors of skin-tumor promotion, I. Inhibitory effects of triterpenes from Euptelea polyandra on Epstein-Barr virus activation." *J. Nat. Prod.* Nov.-Dec. 1987;50(6):1167-70.

Noda et al. "Enhanced cytotoxicity of some triterpenes toward leukemia L1210 cells cultured in low pH media: possibility of a new mode of cell killing." *Chem. Pharm. Bull.* (Tokyo). Oct. 1997;45(10):1665-70.

Pouzar et al. "Preparation of 12,20-disubstituted lupine derivatives." *Collection Czechoslov. Chem. Commun.* 1979;44;194-210.

Ryu et al. "Antitumor triterpenes from medicinal plants." *Arch. Pharr. Res.* 1994;17(5):375-377.

Sejbal et al. "Functionalization of 3β,28-lupanediol diacetate with chromium(vi) oxide." *Collect. Czech. Chem. Commun.* 1991;56:2936-2949.

Suokas et al. "Triterpenes. A novel acid catalysed double bond migration in 3β,28-diacetoxy-lup-20(30)-ene (Betulin diacetate)." *Acta. Chem. Scand.* 1975;B29:139-140.

Yasukawa et al. "Some lupine-type triterpenes inhibit tumor promotion by 12-*O*-tetradecanoylphorbol-13-acetate in two-stage carcinogenesis in mouse skin." *Phytomedicine* 1995;4:309-313.

Klinotová, Eva et al., "Oxidation of 3β,28-Diacetoxy-18-Lupen-21-One with Peroxy Acids: A Way to Des-E-Lupane Derivatives," *Collect. Czech. Chem. Commun.*, vol. 58:2505-2516 (1993).

Šarek, Jan et al., "Štěpení Dvojně Vazby V Derivátech 18-Lupenu Oxidem Ruthenićelym—Cesta K Des-E-Lupanovym Sloučeninăm,"*Lab. Exp. Mediciny*, vol. 11:1005-1006 (1997).

Šarek, J. et al., "Splitting of the Double Bond in 18-Lupinine Derivatives Using Ruthenium (VIII) Oxide—The Route to Des-E-Lupanine Compounds,", 1997.

* cited by examiner

TRITERPENOID DERIVATIVES

RELATED APPLICATIONS

This application is a 35 U.S.C. 371 filing of International Application Number PCT/GB01/02309 which was filed 23 May 2001, which claims priority to Great Britain Publication 0012528.6, filed 23 May 2000 in Great Britain, and 0012823.1, filed 25 May 2000 in Great Britain. The contents of the aforementioned applications are hereby incorporated by reference.

The present invention relates to the therapeutic use and the biological activity of triterpenoid derivatives. The invention further relates to novel triterpenoid derivatives.

To date, the prior art has primarily focussed on compounds that are capable of regulating the cell cycle by virtue of inhibiting cyclin dependent kinases (CDKs). Examples of such compounds include butyrolactone I, flavopiridol, bohemin, olomoucine, roscovitine, purvanalol and indarubicine.

There is considerable support in the literature for the hypothesis that CDKs and their regulatory proteins play a significant role in the development of human tumours. Thus, in many tumours a temporal abnormal expression or activity of CDKs has been observed, together with a major deregulation of protein inhibitors (mutations, deletions). This results in the activation of CDKs and consequently in defective regulation of the G1/S transition. Unlike normal cells, tumour cells do not arrest in G1, and since they become independent of growth factors, they pass the G1 restriction point and enter the S phase very rapidly.

In contrast to the prior art, the present invention relates to compounds which are anti-proliferative, but which are believed to operate via a mechanism other than CDK inhibition.

The $G_1$/S transition of the mammalian cell cycle is tightly regulated by the retinoblastoma protein (pRb). Retinoblastoma gene mutations or deletions predispose individuals to familiar retinoblastoma and other types of cancers. The pRb protein is a docking protein, which in hypophosphorylated form has the capacity to bind and thus to inactivate S-phase transcription factors such as DP-1 and E2F. However, following phosphorylation by G1/S cyclin-dependent kinases (CDKs) (CDK4/cyclin D1-D3, CDK6/cyclin D1-D3, CDK2/cyclin A), hyperphosphorylated pRb releases the transcription factors and S phase is initiated. Within the S phase, the pRb protein phosphorylation is maintained by the activity of CDK2/cyclin E complexes. Thus, hyperphosphorylation of the pRb protein plays a key role in the molecular pathology of cancer cells with altered CDK activity.

The present invention relates to the use of triterpenoid compounds derived from the natural products betulin and betulinic acid (BA) as shown in formula (A). The compounds of the present invention are referred to hereinafter as betulinines.

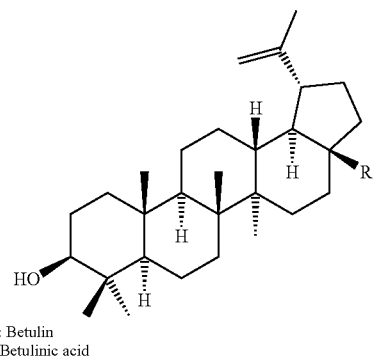

(A)

R = $CH_2OH$: Betulin
R = COOH: Betulinic acid

With regard to their biological and therapeutic activity, the compounds disclosed herein are believed to be of specific benefit in the treatment of proliferative diseases such as cancers and leukaemias.

Several of the compounds suitable for use in the present invention are already known in the art, for example those disclosed in Ber. Dtsch. Chem. Ges. 55, 2332 (1922), Schulze H. et al; Acta Chem. Scand., B 29, 139 (1975), Suokas E. et al; Collect. Czech Chem. Commun. 56, 2936 (1991), Sejbal J. et al; Collect. Czech. Chem. Commun. 64, 329 (1999), Klinotová E. et al; Indian. J. Chem., Sect. B 34, 624 (1995), Dinda B. et al. However, these disclosures do not include any indication as to possible biological activity of such compounds.

A first aspect of the present invention relates to the use of a compound of formula I, or a pharmaceutically acceptable salt thereof, in therapy, in therapy,

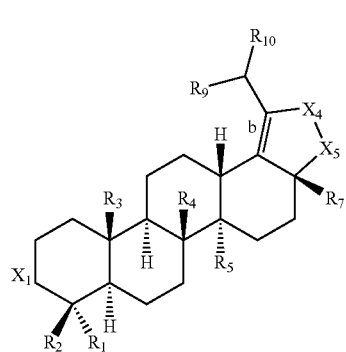

I wherein:
$X^1$ is C=O, C=$NOR^{1a}$, $CHOR^{1a}$, $CHOCOR^{1a}$, CHOC(O)$OR^{11}$, CHOC(O)$OR^{1a}$, CHOC(O)$OR^{12}$, or CHOCOY-Hal $X^4$ is $CH_2$, CH-Hal, C=O, $CHOR^{1b}$, $CHOCOR^{1b}$, CHOC(O)$OR^{11}$ $X^5$ is $CH_2$, CH-Hal, C=O, $CHOR^{1b}$, $CHOCOR^{1b}$, CHOC(O)$OR^{11}$ $R^{1-5}$ are H or lower alkyl $R^7$ is $COOR^{1c}$, $COOR^{12}$, COHal, C(O)OC(O)$R^{1c}$, COOYOCOR$^{1c}$, $CH_2OR^{1c}$, $CH_2OCOR^{1c}$, $CH_2OC(O)OR^{11}$ $R^9$ is $R^{1d}$, $OR^{1d}$, $CH_2$-Hal, $CH_2OR^{1d}$, $CH_2OC(O)OR^{11}$, =$CHR^{1d}$ $R^{10}$ is $R^{1e}$, CH=$NOR^{1e}$, CN, $COOR^{1e}$, $COR^{1e}$, $CH_2$-Hal, $CH_2OR^{1e}$, $CH_2OCOR^{1e}$, $CH_2OC(O)OR^{11}$, $CH_2OSO_2CH_3$, $CH_2OSO_2C_6H_4CH_3$ $R^{11}$ is an OH-substituted alkyl group, an ether group or a cyclic ether, $R^{12}$ is lower alkyl substituted by Hal
"b" is a double bond or a single bond
and wherein $Y=(CH_2)n$
  n=0 to 5
  $R^{1a-1e}$ are the same or different groups of $R^1$
  Hal is Cl, Br, I, F;

with the proviso that said compound is other than
3β-3-hydroxylup-20(29)-en-28-oic acid;
3β-lup-20(29)-ene-3,28-diol;
3β-lup-20(29)-ene3,28-diol diacetate;
3β-3-(acetyloxy)lup-20(29)-en-28-oic acid;
3β-3-(1-oxobutoxy)lup-20(29)-en-28-oic acid;
3β-lup-20(29)-ene-3,28-diol 3-acetate;
3β-lup-20(29)-ene-3,28-diol 28-acetate;
3β-3-hydroxylup-20(29)-en-28-oic acid methyl ester;
3β-3-(acetyloxy)lup-20(29)-en-28-oic acid methyl ester;
3β-3-hydroxylup-20(29)-en-28-oic acid ethyl ester;
3β-3-hydroxylup-20(29)-en-28-oic acid butyl ester;
3β-lupane-3,28-diol;
3β-3-hydroxylupan-28-oic acid;
3β-3-hydroxylupan-28-oic acid methyl ester;
3β-3-(acetyloxy)lupan-28-oic acid methyl ester,
3β-3-(acetyloxy)lupan-28-oic acid;
3β-lupane-3,28-diol diacetate;
3β-lupane-3,28-diol dibutanoate;
3β-3-(3-methyl-1-oxobutoxy)lupan-28-oic acid;
3β-3-(2,2-dimethyl-1-oxopropoxy)lupan-28-oic acid;
3β-3,28-dimethoxylup-20(29)-ene;
3β-3,28-dimethoxylupane;
3β-28-methoxylupan-3-ol;
3β-3-methoxylup-20(29)en-28-oic acid;
3β-3-methoxylup-20(29)-en-28-oic acid methyl ester;
3α-3-methoxylup-20(29)-en-28-oic acid; or
3α-3-methoxylup-20(29)-en-28-oic acid methyl ester.

In a preferred aspect, the invention relates to the use of a compound of formula I, or a pharmaceutically acceptable salt thereof, for treating a patient suffering from leukaemia, cancer or other proliferative disorder.

A second aspect of the present invention relates to novel betulinines of structural formula Ia, or a pharmaceutically acceptable salt thereof, Ia

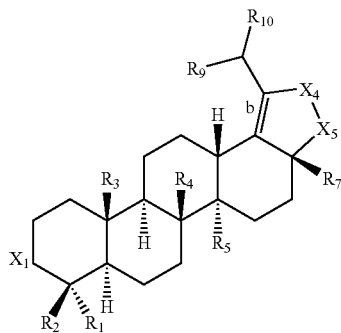

wherein:
$X^1$ is $CHOC(O)OR^{11}$, $CHOC(O)OR^{1a}$, $CHOC(O)OR^{12}$, or CHOCOY-Hal
$X^4$ is $CH_2$, CH-Hal, C=O, $CHOR^{1b}$, $CHOCOR^{1b}$, $CHOC(O)OR^{11}$
$X^5$ is $CH_2$, CH-Hal, C=O, $CHOR^{1b}$, $CHOCOR^{1b}$, $CHOC(O)OR^{11}$
$R^{1-5}$ are H or lower alkyl
$R^7$ is COHal, $C(O)OC(O)R^{1c}$, $COOYOCOR^{1c}$, $CH_2OC(O)OR^{11}$ $R^9$ is $R^{1d}$, $OR^{1d}$, $CH_2$-Hal, $CH_2OR^{1d}$, $CH_2OC(O)OR^{11}$, $=CHR^{1d}$
$R^{10}$ is $R^{1e}$, $CH=NOR^{1e}$, CN, $COOR^{1e}$, $COR^{1e}$, $CH_2$-Hal, $CH_2OR^{1e}$, $CH_2OCOR^{1e}$, $CH_2OC(O)OR^{11}$, $CH_2OSO_2CH_3$, $CH_2OSO_2C_6H_4CH_3$
$R^{11}$ is an OH-substituted alkyl group, an ether group or a cyclic ether;
$R^{12}$ is lower alkyl substituted by Hal
"b" is a double bond or a single bond
and wherein $Y=(CH_2)n$
  n=0 to 5
  $R^{1a-1e}$ are the same or different groups of $R^1$
  Hal is Cl, Br, I, F.

As used herein, the term lower alkyl means a linear or branched chain alkyl group containing from 1 to 6 carbon atoms, including methyl, ethyl, propyl, isopropyl, butyl, isobutyl, tertiary butyl.

DESCRIPTION OF THE PREFERRED EMBODIMENTS

Within the options provided for the groups $X^1$, $X^4$, $X^5$ and $R^{1-5}$, $R^7$, $R^{9-10}$ of formula I, the following options are preferred;

$X^1$ is C=O, $CHOR^{1a}$, $CHOCOR^{1a}$, CHOCOY-Hal, $CHOCOOR^{11}$;

$X^4$ is C=O, $CH_2$;

$X^5$ is C=O, $CH_2$, $CHOCOR^{1b}$;

$R^7$ is $COOR^{1c}$, $CH_2OR^{1c}$, $CH_2OCOR^{1c}$, $COOYOCOR^{1c}$, $CH_2OSO_2C_6H_4CH_3$, COHal, $COOCOR^{1c}$, $CH_2OCOOR^{11}$;

$R^9$ is $R^{1d}$, $=CHR^{1d}$, $CH_2OR^{1d}$, $OR^{1d}$;

$R^{10}$ is $R^{1e}$, CN, $COOR^{1e}$, $CH_2OR^{1e}$, $COR^{1e}$.

Preferably, $R^{11}$ is a diol, triol or polyol.

Even more preferably, $R^1$, $R^{3-5}$ are methyl, $R^2$ is H or methyl, and $R^1$ is defined as below for the relevant group $R^{1a-e}$;

when $X^1$ is:
  —$CHOR^{1a}$, $R^{1a}$ is H;
  —CHCOY-Hal, Y is $CH_2$ and Hal is Cl;
  —$CHOCOR^{1a}$, $R^{1a}$ is methyl;
  —$CHOCOOR^{11}$, $R^{11}$ is glyceryl, 2,2-dimethyl-1,3-dioxolan-4-yl or pentaerythrityl;

when $X^5$ is $CHOCOR^{1b}$, $R^{1b}$ is methyl;

when $R^7$ is:
  —$COOR^{1c}$, $R^{1c}$ is H or methyl;
  —$COOYOCOR^{1c}$, Y is $CH_2$ and $R^{1c}$ is H;
  —$CH_2OR^{1c}$, $R^{1c}$ is H;
  —$CH_2OCOR^{1c}$, $R^{1c}$ is methyl;
  —$COOCOR^{1c}$, $R^{1c}$ is methyl or butyl;
  —COHal, Hal is Cl;
  —$CH_2OCOOR^{11}$, $R^{11}$ is glyceryl, 2,2-dimethyl-1,3-dioxolan-4-yl or pentaerythrityl;

when $R^9$ is $=CHR^{1d}$, $CH_2OR^{1d}$ or $OR^{1d}$, $R^{1d}$ is H, and when $R^9$ is $R^{1d}$, $R^{1d}$ is methyl;

when $R^{10}$ is $R^{1e}$, $R^{1e}$ is methyl, and when $R^{10}$ is $COOR^{1e}$, $COR^{1e}$ or $CH_2OR^{1e}$, $R^{1e}$ is H.

In a more preferred embodiment of the first aspect of the invention, the compounds of use are selected from those shown in Table 1 below.

TABLE 1

| No. | $X^1$ | $X^4$ | $X^5$ | b | $R^{1-5}$ | $R^7$ | $R^9$ | $R^{10}$ |
|---|---|---|---|---|---|---|---|---|
| II.1 | CHOAc | C=O | $CH_2$ | double | Me | COOH | Me | Me |
| II.2 | CHOAc | C=O | C=O | double | Me | $CH_2OAc$ | Me | Me |
| II.3 | CHOAc | C=O | $CH_2$ | double | Me | $CH_2OAc$ | Me | Me |
| II.4 | CHOAc | C=O | C=O | double | Me | COOMe | Me | Me |
| II.5 | $CHOCOCH_2Cl$ | C=O | $CH_2$ | double | Me | $CH_2OAc$ | Me | Me |
| II.6 | $CHOCOCH_2Cl$ | C=O | C=O | double | Me | $CH_2OAc$ | Me | Me |
| II.7 | CHOH | C=O | C=O | double | Me | $CH_2OAc$ | Me | Me |
| II.8 | CHOH | C=O | C=O | double | Me | $CH_2OH$ | Me | Me |
| II.9 | CHOAc | C=O | $CH_2$ | double | Me | $COOCH_2O—COBu^t$ | Me | Me |
| II.10 | CHOAc | C=O | $CH_2$ | double | Me | COOMe | Me | Me |
| II.11 | CHOAc | C=O | C=O | double | Me | $COOCH_2OCOBu^t$ | Me | Me |
| II.12 | CHOAc | $CH_2$ | $CH_2$ | single | Me | COOH | $CH_2$ | CN |
| II.13 | CHOAc | $CH_2$ | $CH_2$ | single | Me | COOH | $CH_2$ | COOH |
| II.14 | CHOH | $CH_2$ | $CH_2$ | single | Me | COOH | $CH_2$ | COH |
| II.15 | CHOAc | $CH_2$ | $CH_2$ | single | Me | COOH | $CH_2$ | $CH_2OH$ |
| II.16 | CHOAc | C=O | CHOAc | double | Me | $CH_2OAc$ | Me | Me |
| II.17 | C=O | $CH_2$ | $CH_2$ | single | Me, ($R^2$:H) | $CH_2OAc$ | Me | Me |
| II.18 | CHOAc | $CH_2$ | $CH_2$ | single | Me | COOH | $CH_2$ | COH |
| II.19 | CHOH | $CH_2$ | $CH_2$ | single | Me | COOH | (20-R)—OH | Me |
| II.20 | CHOH | $CH_2$ | $CH_2$ | single | Me | COOH | (20-S)—OH | Me |
| II.21 | CHOH | $CH_2$ | $CH_2$ | single | Me | COOH | (20-R)—$CH_2OH$ | Me |
| II.22 | CHOH | $CH_2$ | $CH_2$ | single | Me | COOH | (20-S)—$CH_2OH$ | Me |
| II.23 | CHOAc | C=O | C=O | double | Me | $COOCH_2OCOMe$ | Me | Me |
| II.24 | CHOH | $CH_2$ | $CH_2$ | single | Me | $COOCH_2OCOBu^t$ | $CH_2$ | COH |
| II.25 | CHOH | $CH_2$ | $CH_2$ | single | Me | $COOCH_2OCOMe$ | $CH_2$ | COH |
| II.26 | CHOH | C=O | C=O | double | Me | COOMe | Me | Me |
| II.27 | CHOH | C=O | $CH_2$ | double | Me | $COOCH_2OCOBu^t$ | Me | Me |
| II.28 | CHOH | C=O | $CH_2$ | double | Me | COOH | Me | Me |
| II.29 | CHOH | C=O | $CH_2$ | double | Me | $CH_2OH$ | Me | Me |
| II.30 | CHOH | C=O | $CH_2$ | double | Me | $CH_2OAc$ | Me | Me |
| II.31 | CHOH | C=O | $CH_2$ | double | Me | COOMe | Me | Me |
| II.32 | CHOH | C=O | $CH_2$ | double | Me | $COOCH_2OCOMe$ | Me | Me |
| II.33 | CHOAc | C=O | $CH_2$ | double | Me | $CH_2OH$ | Me | Me |
| II.34 | A | C=O | $CH_2$ | double | Me | COOMe | Me | Me |
| II.35 | B | C=O | $CH_2$ | double | Me | COOMe | Me | Me |
| II.36 | CHOAc | C=O | C=O | double | Me | $CH_2OH$ | Me | Me |
| II.37 | CHOH | C=O | C=O | double | Me | $COOCH_2OCOMe$ | Me | Me |
| II.38 | CHOH | C=O | C=O | double | Me | $COOCH_2OCOBu^t$ | Me | Me |
| II.39 | A | C=O | C=O | double | Me | COOMe | Me | Me |
| II.40 | B | C=O | C=O | double | Me | COOMe | Me | Me |
| II.41 | A | C=O | $CH_2$ | double | Me | COOH | Me | Me |
| II.42 | B | C=O | $CH_2$ | double | Me | COOH | Me | Me |
| II.43 | A | $CH_2$ | $CH_2$ | single | Me | COOH | $CH_2$ | Me |
| II.44 | B | $CH_2$ | $CH_2$ | single | Me | COOH | $CH_2$ | Me |
| II.45 | A | $CH_2$ | $CH_2$ | single | Me | COOMe | $CH_2$ | Me |
| II.46 | B | $CH_2$ | $CH_2$ | single | Me | COOMe | $CH_2$ | |
| II.47 | A | $CH_2$ | $CH_2$ | single | Me | $COOCH_2OCOMe$ | $CH_2$ | Me |
| II.48 | B | $CH_2$ | $CH_2$ | single | Me | $COOCH_2OCOMe$ | $CH_2$ | Me |
| II.49 | CHOAc | $CH_2$ | $CH_2$ | single | Me | $CH_2OTs$ | $CH_2$ | Me |
| II.50 | A | $CH_2$ | $CH_2$ | single | Me | HA | $CH_2$ | Me |
| II.51 | B | $CH_2$ | $CH_2$ | single | Me | HB | $CH_2$ | Me |
| II.52 | CHOAc | $CH_2$ | $CH_2$ | single | Me | COOCOMe | $CH_2$ | COH |
| II.53 | CHOAc | $CH_2$ | $CH_2$ | single | Me | COOCOMe | $CH_2$ | Me |
| II.54 | CHOAc | C=O | $CH_2$ | double | Me | COF | Me | Me |
| II.55 | CHOAc | $CH_2$ | $CH_2$ | single | Me | COF | $CH_2$ | Me |
| II.56 | CHOAc | $CH_2$ | $CH_2$ | single | Me | COF | $CH_2$ | COH |
| II.57 | C=O | $CH_2$ | $CH_2$ | single | Me | COF | $CH_2$ | Me |
| II.58 | CHOAc | $CH_2$ | $CH_2$ | single | Me | COF | Me | Me | where: A is $CHOC(O)OCH_2CHOHCH_2OH$
B is $CHOC(O)OCH_2$-2,2-dimethyl-1,3-dioxolan-4-yl
Ts is $OSO_2C_6H_4CH_3$.

In a particularly preferred embodiment, said compound is selected from the following:

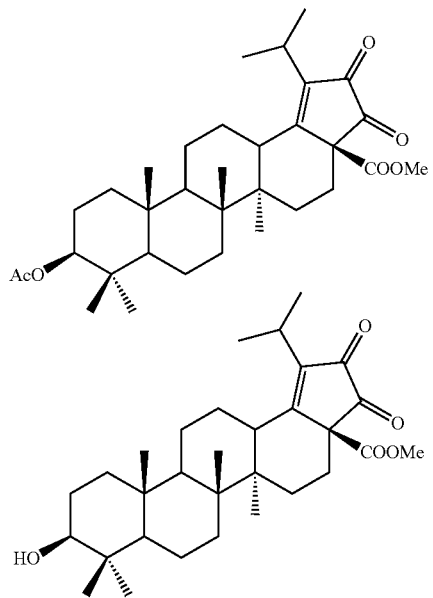

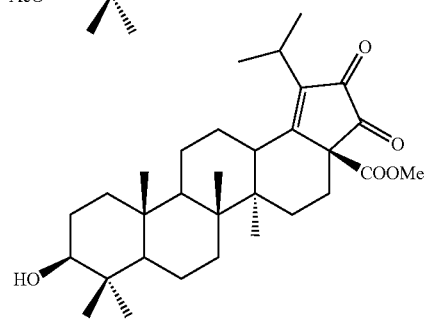

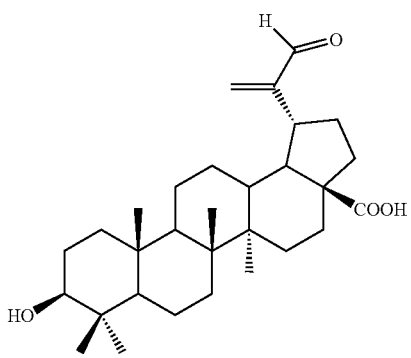

In respect of the second aspect of the invention, the preferred embodiments regarding the compounds are identical to those given above for the first aspect with application of the proviso of formula Ia.

The most preferred compounds of the second aspect are those in Table 1a.

TABLE 1a

| No. | $X^1$ | $X^4$ | $X^5$ | b | $R^{1-5}$ | $R^7$ | $R^9$ | $R^{10}$ |
|---|---|---|---|---|---|---|---|---|
| II.1 | CHOAc | C=O | $CH_2$ | double | Me | COOH | Me | Me |
| II.4 | CHOAc | C=O | C=O | double | Me | COOMe | Me | Me |
| II.5 | CHOCOCH$_2$Cl | C=O | $CH_2$ | double | Me | $CH_2OAc$ | Me | Me |
| II.6 | CHOCOCH$_2$Cl | C=O | C=O | double | Me | $CH_2OAc$ | Me | Me |
| II.7 | CHOH | C=O | C=O | double | Me | $CH_2OAc$ | Me | Me |
| II.8 | CHOH | C=O | C=O | double | Me | $CH_2OH$ | Me | Me |
| II.9 | CHOAc | C=O | $CH_2$ | double | Me | COOCH$_2$O—COBu$^t$ | Me | Me |
| II.11 | CHOAc | C=O | C=O | double | Me | COOCH$_2$OCOBu$^t$ | Me | Me |
| II.12 | CHOAc | $CH_2$ | $CH_2$ | single | Me | COOH | $CH_2$ | CN |
| II.13 | CHOAc | $CH_2$ | $CH_2$ | single | Me | COOH | $CH_2$ | CO |
| II.15 | CHOAc | $CH_2$ | $CH_2$ | single | Me | COOH | $CH_2$ | $CH_2OH$ |
| II.16 | CHOAc | C=O | CHOAc | double | Me | $CH_2OAc$ | Me | Me |
| II.17 | C=O | $CH_2$ | $CH_2$ | single | Me, ($R^2$:H) | $CH_2OAc$ | Me | Me |
| II.18 | CHOAc | $CH_2$ | $CH_2$ | single | Me | COOH | $CH_2$ | COH |
| II.19 | CHOH | $CH_2$ | $CH_2$ | single | Me | COOH | (20-R)—OH | Me |
| II.20 | CHOH | $CH_2$ | $CH_2$ | single | Me | COOH | (20-S)—OH | Me |
| II.21 | CHOH | $CH_2$ | $CH_2$ | single | Me | COOH | (20-R)—CH$_2$OH | Me |
| II.22 | CHOH | $CH_2$ | $CH_2$ | single | Me | COOH | (20-S)—CH$_2$OH | Me |
| II.23 | CHOAc | C=O | C=O | double | Me | COOCH$_2$OCOMe | Me | Me |
| II.24 | CHOH | $CH_2$ | $CH_2$ | single | Me | COOCH$_2$OCOBu$^t$ | $CH_2$ | COH |
| II.25 | CHOH | $CH_2$ | $CH_2$ | single | Me | COOCH$_2$OCOMe | $CH_2$ | COH |
| II.26 | CHOH | C=O | C=O | double | Me | COOMe | Me | Me |
| II.27 | CHOH | C=O | $CH_2$ | double | Me | COOCH$_2$OCOBu$^t$ | Me | Me |
| II.30 | CHOH | C=O | $CH_2$ | double | Me | $CH_2OAc$ | Me | Me |
| II.31 | CHOH | C=O | $CH_2$ | double | Me | COOMe | Me | Me |
| II.32 | CHOH | C=O | $CH_2$ | double | Me | COOCH$_2$OCOMe | Me | Me |
| II.34 | A | C=O | $CH_2$ | double | Me | COOMe | Me | Me |
| II.35 | B | C=O | $CH_2$ | double | Me | COOMe | Me | Me |
| II.36 | CHOAc | C=O | C=O | double | Me | $CH_2OH$ | Me | Me |
| II.37 | CHOH | C=O | C=O | double | Me | COOCH$_2$OCOMe | Me | Me |
| II.38 | CHOH | C=O | C=O | double | Me | COOCH$_2$OCOBu$^t$ | Me | Me |
| II.39 | A | C=O | C=O | double | Me | COOMe | Me | Me |
| II.40 | B | C=O | C=O | double | Me | COOMe | Me | Me |
| II.41 | A | C=O | $CH_2$ | double | Me | COOH | Me | Me |
| II.42 | B | C=O | $CH_2$ | double | Me | COOH | Me | Me |
| II.43 | A | $CH_2$ | $CH_2$ | single | Me | COOH | $CH_2$ | Me |
| II.44 | B | $CH_2$ | $CH_2$ | single | Me | COOH | $CH_2$ | Me |
| II.45 | A | $CH_2$ | $CH_2$ | single | Me | COOMe | $CH_2$ | Me |
| II.46 | B | $CH_2$ | $CH_2$ | single | Me | COOMe | $CH_2$ | Me |
| II.47 | A | $CH_2$ | $CH_2$ | single | Me | COOCH$_2$OCOMe | $CH_2$ | Me |
| II.48 | B | $CH_2$ | $CH_2$ | single | Me | COOCH$_2$OCOMe | $CH_2$ | Me |
| II.49 | CHOAc | $CH_2$ | $CH_2$ | single | Me | $CH_2OTs$ | $CH_2$ | Me |

TABLE 1a-continued

| No. | $X^1$ | $X^4$ | $X^5$ | b | $R^{1-5}$ | $R^7$ | $R^9$ | $R^{10}$ |
|---|---|---|---|---|---|---|---|---|
| II.50 | A | $CH_2$ | $CH_2$ | single | Me | HA | $CH_2$ | Me |
| II.51 | B | $CH_2$ | $CH_2$ | single | Me | HB | $CH_2$ | Me |
| II.52 | CHOAc | $CH_2$ | $CH_2$ | single | Me | COOCOMe | $CH_2$ | COH |
| II.53 | CHOAc | $CH_2$ | $CH_2$ | single | Me | COOCOMe | $CH_2$ | Me |
| II.54 | CHOAc | C=O | $CH_2$ | double | Me | COF | Me | Me |
| II.55 | CHOAc | $CH_2$ | $CH_2$ | single | Me | COF | $CH_2$ | Me |
| II.56 | CHOAc | $CH_2$ | $CH_2$ | single | Me | COF | $CH_2$ | COH |
| II.57 | C=O | $CH_2$ | $CH_2$ | single | Me | COF | $CH_2$ | Me |
| II.58 | CHOAc | $CH_2$ | $CH_2$ | single | Me | COF | Me | Me | where: A is $CHOC(O)OCH_2CHOHCH_2OH$
B is $CHOC(O)OCH_2$-2,2-dimethyl-1,3-dioxolan-4-yl
Ts is $OSO_2C_6H_4CH_3$.

In respect of the invention as a whole, it is preferable that the proliferative disorder is cancer or leukaemia. In one embodiment, the cancer or leukaemia is p53, hormone and multidrug resistance independent. In another embodiment, the cancer or leukaemia is independent of Rb status.

More specifically, the present invention relates to a method of treating patients suffering from cancer by administering therapeutically effective amounts of a compound of formula I or pharmaceutically acceptable salts or esters thereof.

Without wishing to be bound by theory, preliminary studies suggest that rather than influencing the activity of cyclin dependent kinases, the compounds of the present invention appear to operate via an alternative mechanism. In particular, it is believed that the betulinines of the present invention may inhibit cell proliferation and induce cancer cell death in a manner which involves mainly post-translational modifications, namely the phosphorylation, of a key regulatory protein involved in cellular proliferation. More specifically, it is believed that the betulinines of the invention effect a change in the phosphorylation state of the Rb protein. Such a mechanism may be advantageous as it is thought that the compounds of the present invention may be capable of inhibiting cell proliferation in proliferating tumour tissue, but not in healthy tissue.

Thus, in a further embodiment the present invention relates to a method of treating a cancerous or leukaemic proliferative disease through effecting a change in the pRb protein phosphorylation state by the administration of a therapeutically effective amount of a compound of formula I or pharmaceutically acceptable salts or esters thereof.

The compounds of the present invention are also capable of inducing apoptosis (programmed cell death) in proliferative cells. Thus, in an additional embodiment, the present invention relates to a method of inducing cell death in proliferative cells comprising administering a therapeutically effective amount of a compound of formula I or pharmaceutically acceptable salts or esters thereof.

A further aspect of the present invention relates to use of betulinines of formula I as research chemicals and as compounds for clinical and/or laboratory diagnostics. More particularly, the invention relates to the use of betulinines as research chemicals for studying the phosphorylation/dephosphorylation processes of cellular substrates, cellular proliferation, purification of target molecules, and/or cell cycle studies.

The present invention therefore further relates to the use of a compound of formula I in the manufacture of a medicament for use in the treatment of a proliferative disease.

As used herein the phrase "manufacture of a medicament" includes the use of a compound of formula I directly as the medicament in addition to its use in a screening programme for further anti-proliferative agents or in any stage of the manufacture of such a medicament.

Such a screening programme may for example include an assay for determining the phosphorylation state of cellular substrates and determining whether a candidate substance is capable of mimicking the activity of a betulinine of formula I.

Thus, in a further embodiment, the invention relates to the use of a compound of formula I or a pharmaceutically acceptable salt, crystal form, complex, hydrate, or hydrolysable ester thereof, in an assay for determining the phosphorylation state of cellular substrates, and optionally in the identification of candidate compounds that act in a similar manner.

Preferably, the cellular substrate, the phosphorylation state of which is being assayed is Rb protein.

Such assays may be carried out by incubating a betulinin either alone or together with a candidate substance with a relevant cell line and assessing the phosphorylation profile the Rb protein over a period of time. If a candidate substance is present it's effect on the activity of the control betulinin will be evident by running the corresponding controls (betulinin alone and candidate alone). Further information on such assays including appropriate cell lines, reagents and Rb antibodies is given below.

Rb phosphorylation assay;

Since Rb protein contains multiple phosphorylation sites for CDKs, its phosphorylated form has molecular weight about 110 kDa, while the molecular weight of hypophosphorylated protein is only 105 kDa. This small difference in molecular weight is enough to separate both forms by conventional SDS-PAGE electrophoresis.

CEM cells may are cultured in Dulbeco's modified essential medium with 4.5 g dextrose/l, 10% of foetal calf serum, 2 mM glutamine, 100 U/ml penicillin and 100 µg/ml streptomycin with/without below indicated concentrations of betulinin. At selected time points, cells are harvested, washed in ice cold Hank's balanced salt solution and solubilized on ice using the SDS-PAGE sample buffer containing protease and phosphatase inhibitors (10 µg/ml of leupeptin, 10 µg/ml of aprotinin, 10 µg/ml of soybean typsin inhibitor, 100 µmol of benzamide, 1 mM of sodium vanadate, 1 mM of NaF, 1 mM of phenylphosphate) and boiled immediately.

Total cellular proteins (100 µg/well) are separated on SDS-PAGE electrophoresis, blotted on polyvinyldifluoride membranes and total Rb protein, including proteolytic fragment(s) detected using a pRb monoclonal antibody (Oncogene, Germany, Rb(Ab-5), Cat #OP66 Rev 2 Sep. 1996 EB, Clone LM95.1) and visualized by chemiluminescence (ECL-Western Blotting System, Amersham). Details of the Western blot technique are described in Ausubel, F. M., Brent, R., Kingston, R. E., Moore, D. D., Seidman, J. G., Smith, J. A., Struhl, K ads): Short Protocols in Molecular Biology, 2nd edition, John Wiley & Sons, New York, Chichester, Brisbane, Toronto, Singapore, 1992, page 10-33-10-35.

The compounds of the present invention can be present as salts or esters, in particular pharmaceutically acceptable salts or esters.

Pharmaceutically acceptable salts of the product of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

In all aspects of the present invention previously discussed, the invention includes, where appropriate all enantiomers and tautomers of compounds of formula I or Ia. The man skilled in the art will recognise compounds that possess optical properties (one or more chiral carbon atoms) or tautomeric characteristics. The corresponding enantiomers and/or tautomers may be isolated/prepared by methods known in the art.

The invention furthermore relates to the compounds of, or of use, in the present invention in their various crystalline forms, polymorphic forms and (an)hydrous forms. It is well established within the pharmaceutical industry that chemical compounds may be isolated in any of such forms by slightly varying the method of purification and or isolation from the solvents used in the synthetic preparation of such compounds.

The invention further includes the compounds of, or of use, in the present invention in prodrug form. Such prodrugs are generally compounds of formula I or Ia wherein one or more appropriate groups have been modified such that the modification is reversed upon administration to a human or mammalian subject. Such reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

The present invention also encompasses pharmaceutical compositions comprising the compounds of the invention. In this regard, and in particular for human therapy, even though the compounds of the present invention (including their pharmaceutically acceptable salts, esters and pharmaceutically acceptable solvates) can be administered alone, they will generally be administered in admixture with a pharmaceutical carrier, excipient or diluent selected with regard to the intended route of administration and standard pharmaceutical practice.

Thus, the present invention also relates to pharmaceutical compositions comprising betulinines or pharmaceutically acceptable salts or esters thereof, together with at least one pharmaceutically acceptable excipient, diluent or carrier.

By way of example, in the pharmaceutical compositions of the present invention, the compounds of the invention may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of malignancy.

The invention further relates to methods of chemical synthesis of the above described compounds.

In one embodiment, the invention relates to a process for preparing a compound of formula I, as defined above, wherein $X^4$ is C=O and $X^5$ is C=O or $CH_2$,

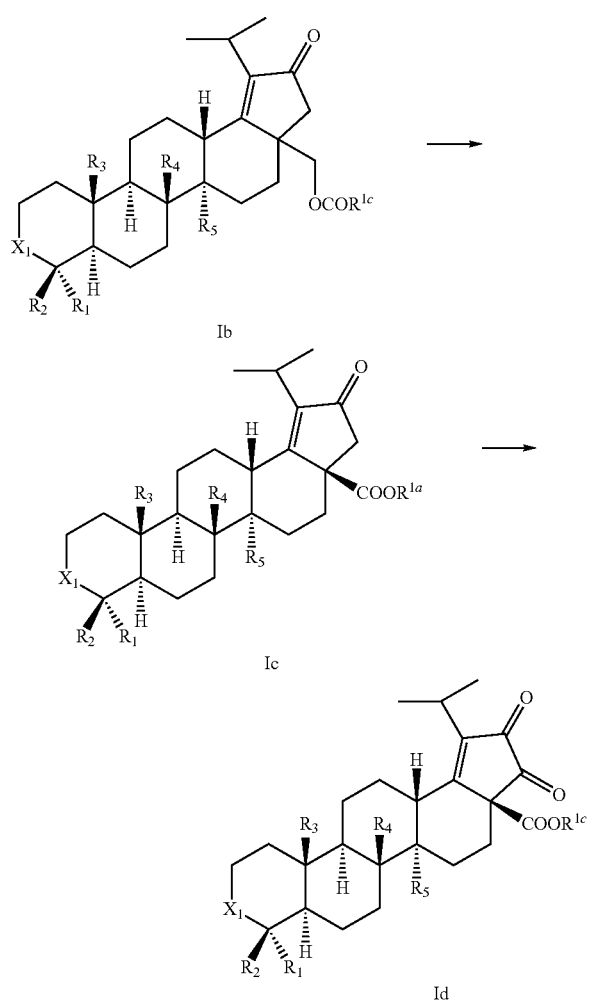

comprising
(i) oxidising a compound of formula Ib to form a compound of formula Ic; and
(ii) where $R^{1c}$ is H, esterifying with an appropriate group bearing the desired $R^{1c}$ substituent; and optionally
(iii) oxidising the product of step (i) or (ii) to form a compound of formula Id.

In a preferred embodiment, the compound of formula Ib is oxidised to Ic by treating with ruthenium tetroxide.

In a preferred aspect, the compound of formula Ic is oxidised to Id by treating with selenium dioxide.

A further embodiment of the invention relates to a process for preparing a compound of formula I as defined above, wherein $X^4$ and $X^5$ are $CH_2$, comprising oxidising a compound of formula Ie to form a compound of formula If.

In a preferred aspect, the compound of formula Ie is oxidised to If by treating with selenium dioxide.

The preparation of the compounds of the present invention will be discussed in greater detail below, with specific reference to the preferred embodiments. The man skilled in the relevant art would be able to prepare other compounds of the invention by selection of the appropriate reagents.

The following scheme illustrates the synthesis of compounds of formula I where $X^1$ is CHOAc, $X^4$ is C=O, $X^5$ is $CH_2$ or C=O, $R^{1-5,9,10}$ are methyl, and $R^7$ is $CH_2OAc$, COOMe or $COOCH_2OCOC(CH_3)_3$.

-continued

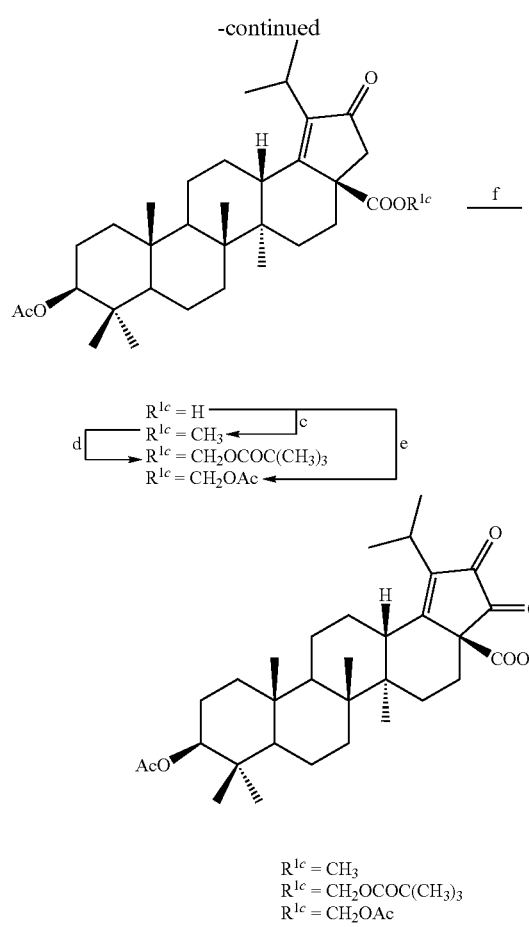

Conditions: a, hydrolysis (e.g. with potassium hydroxide); b, oxidation (e.g. with ruthenium tetroxide); c, esterification (e.g. with diazomethane); d, esterification with POM-Cl in the presence of base (e.g. DBU); e, esterification with AcM-Br in the presence of base (e.g. DBU); f, oxidation (e.g. with selenium dioxide).

The scheme below illustrates the synthesis of compounds of formula I where $X^1$ is CHOAc, $X^{4,5}$ are $CH_2$, $R^{1-5}$ are methyl, $R^7$ is COOH, $R^9$ is $CH_2$, and $R^{10}$ is COH.

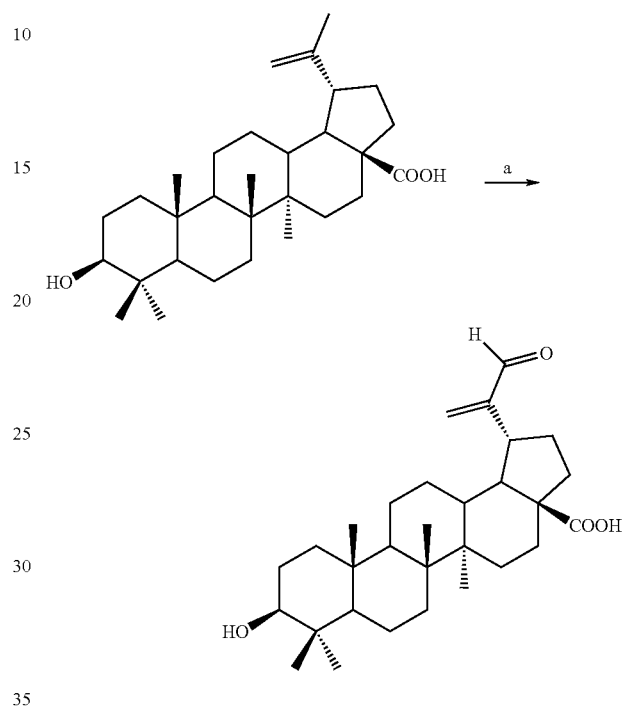

Conditions: a, oxidation (e.g. with selenium dioxide).

The scheme below illustrates the synthesis of compounds II.34, II.35, II.39-II.48, II.50 and II.51 of formula I where $R^{1-5}$ are methyl.

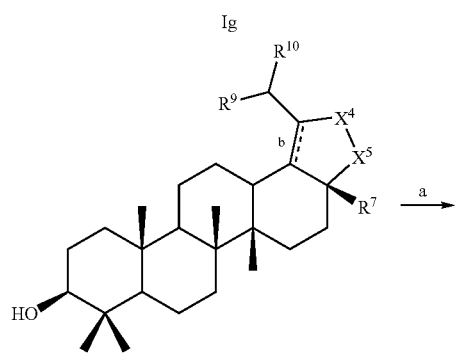

$X^4 = C=O, X^5 = CH_2$
$R^9 = CH_3, R^{10} = CH_3$
$R^7 = COOCH_3$
b is double bond
or
$X^4 = C=O, X^5 = CH_2$
$R^9 = CH_3, R^{10} = CH_3$
$R^7 = COOH$
b is double bond or
$X^4$ = C=O, $X^5$ = C=O
$R^9$ = CH$_3$, $R^{10}$ = CH$_3$
$R^7$ = COOCH$_3$
b is double bond
or
$X^4$ = CH$_2$, $X^5$ = CH$_2$
$R^9$ = =CH$_2$, $R^{10}$ = CH$_3$
$R^7$ = COOH
b is single bond
or
$X^4$ = CH$_2$, $X^5$ = CH$_2$
$R^9$ = =CH$_2$, $R^{10}$ = CH$_3$
$R^7$ = OOOCH$_3$
b is single bond
or
$X^4$ = CH$_2$, $X^5$ = CH$_2$
$R^9$ = =CH$_2$, $R^{10}$ = CH$_3$
$R^7$ = COOCH$_2$OCOCH$_3$
b is single bond
or
$X^4$ = CH$_2$, $X^5$ = CH$_2$
$R^9$ = =CH$_2$, $R^{10}$ = CH$_3$
$R^7$ = CH$_2$OH
b is single bond

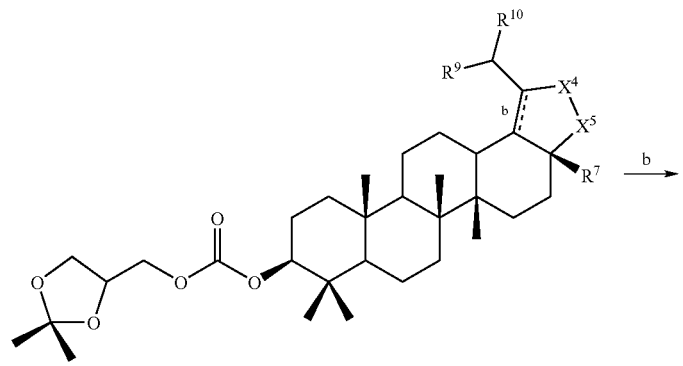

Ih $X^4$ = C=O, $X^5$ = CH$_2$
$R^9$ = CH$_3$, $R^{10}$ = CH$_3$
$R^7$ = COOCH$_3$
b is double bond
or
$X^4$ = C=O, $X^5$ = CH$_2$
$R^9$ = CH$_3$, $R^{10}$ = CH$_3$
$R^7$ = COOH
b is double bond
or
$X^4$ = C=O, $X^5$ = C=O
$R^9$ = CH$_3$, $R^{10}$ = CH$_3$
$R^7$ = COOCH$_3$
b is double bond
or
$X^4$ = CH$_2$, $X^5$ = CH$_2$
$R^9$ = =CH$_2$, $R^{10}$ = CH$_3$
$R^7$ = COOH
b is single bond
or
$X^4$ = CH$_2$, $X^5$ = CH$_2$
$R^9$ = =CH$_2$, $R^{10}$ = CH$_3$
$R^7$ = OOOCH$_3$
b is single bond
or
$X^4$ = CH$_2$, $X^5$ = CH$_2$
$R^9$ = =CH$_2$, $R^{10}$ = CH$_3$
$R^7$ = COOCH$_2$OCOCH$_3$
b is single bond
or
$X^4$ = CH$_2$, $X^5$ = CH$_2$
$R^9$ = =CH$_2$, $R^{10}$ = CH$_3$ -continued R⁷ = 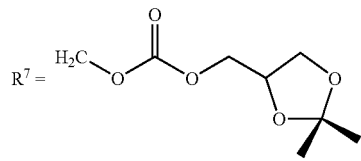

b is single bond

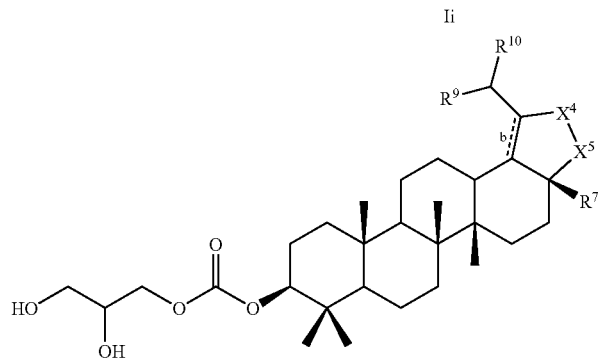

Ii $X^4 = C=O, X^5 = CH_2$
$R^9 = CH_3, R^{10} = CH_3$
$R^7 = COOCH_3$
b is double bond
or
$X^4 = C=O, X^5 = CH_2$
$R^9 = CH_3, R^{10} = CH_3$
$R^7 = COOH$
b is double bond
or
$X^4 = C=O, X^5 = C=O$
$R^9 = CH_3, R^{10} = CH_3$
$R^7 = COOCH_3$
b is double bond
or
$X^4 = CH_2, X^5 = CH_2$
$R^9 = =CH_2, R^{10} = CH_3$
$R^7 = COOH$
b is single bond
or
$X^4 = CH_2, X^5 = CH_2$
$R^9 = =CH_2, R^{10} = CH_3$
$R^7 = OOOCH_3$
b is single bond
or
$X^4 = CH_2, X^5 = CH_2$
$R^9 = =CH_2, R^{10} = CH_3$
$R^7 = COOCH_2OCOCH_3$
b is single bond
or
$X^4 = CH_2, X^5 = CH_2$
$R^9 = =CH_2, R^{10} = CH_3$ R⁷ = 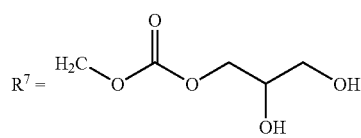

b is single bond

Conditions: a, esterification with chloroformate of solketal in presence of base (e.g. pyridine); b, deprotection of acetonide (e.g. with hydrochloric acid).

The scheme below illustrates the synthesis of compounds II.54-II.58 of formula I where $R^1$-$R^5$ are methyl, $X^5$ is $CH_2$, $X^1$ is CHOAc or C=O, $X^4$ is $CH_2$ or C=O, $R^9$ is =$CH_2$ or $CH_3$, $R^{10}$ is $CH_3$ or COH and $R^7$ is COOH or COF.

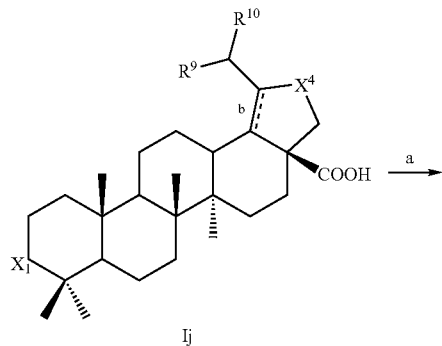

Ij $X^1$ = CHOAc, $X^4$ = $CH_2$
$R^9$ = $CH_2$, $R^{10}$ = $CH_3$
b is single bond
or
$X^1$ = CHOAc, $X^4$ = $CH_2$
$R^9$ = $CH_3$, $R^{10}$ = $CH_3$
b is single bond
or
$X^1$ = C=O, $X^4$ = $CH_2$
$R^9$ = =$CH_2$, $R^{10}$ = $CH_3$
b s single bond
or
$X^1$ = CHOAc, $X^4$ = $CH_2$
$R^9$ = =$CH_2$, $R^{10}$ = COH
b is single bond
or
$X^1$ = CHOAc, $X^4$ = C=O
$R^9$, $R^{10}$ = CH3
b is double bond

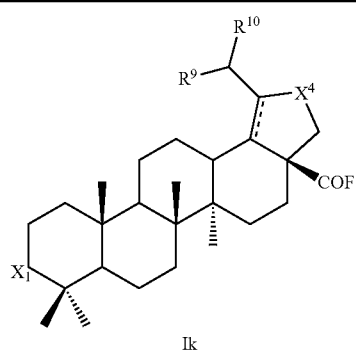

Ik $X^1$ = CHOAc, $X^4$ = $CH_2$
$R^9$ = $CH_2$, $R^{10}$ = $CH_3$
b is single bond
or
$X^1$ = CHOAc, $X^4$ = $CH_2$
$R^9$ = $CH_3$, $R^{10}$ = $CH_3$
b is single bond
or
$X^1$ = C=O, $X^4$ = $CH_2$
$R^9$ = =$CH_2$, $R^{10}$ = $CH_3$
b s single bond
or
$X^1$ = CHOAc, $X^4$ = $CH_2$
$R^9$ = =$CH_2$, $R^{10}$ = COH
b is single bond
or
$X^1$ = CHOAc, $X^4$ = C=O
$R^9$, $R^{10}$ = CH3
b is double bond Conditions: a, reaction with diethylaminosulphur trifluoride.

This invention is further illustrated by the following examples, which should not be construed as further limiting.

EXAMPLES

General

The chemical shift values (δ-scale, ppm) and coupling constants (J, Hz) in the $^1$H and $^{13}$C NMR spectra were obtained using a Varian UNITY-INOVA 400 FT spectrometer ($^1$H at 400 MHz and $^{13}$C at 100.6 MHz) in deuterochloroform with tetramethylsilane (for $^1$H NMR data δ=0 ppm) as an internal standard. For the $^{13}$C NMR data δ(CDCl$_3$)=77.00 ppm. The value for a multiplet, either defined (doublet (d), triplet (t), quartet (q), septet (sept.) or not (m) at the approximate mid point is given unless a range is quoted (s=singlet, b=broad)).

Electron impact mass spectra (EIMS) were measured on an INCOS 50 instrument. Ionising electron energy 75 eV, ion source temperature 150° C. EIMS was used to determine molecular weights, M$^+$ corresponding to the molecular ion.

Ether is diethylether. THF and dioxane were dried over sodium. Acetic acid was purified before use by chromium trioxide treatment and distillation. Reactions were run at room temperature unless otherwise stated. The reaction progress was monitored by thin layer chromatography (TLC) on silicagel 60 G (Merck, detection by spraying with 10% sulphuric acid and heating). The work-up procedure involves dilution with specified solvent (otherwise the organic reaction solvent), extraction with water and then brine or sodium hydrogencarbonate, drying over anhydrous magnesium sulphate, and evaporation under vacuum to give a residue.

Example 1

Lup-20(29)-ene-3β,28-diyl diacetate

Crude betuline (500 g) was dissolved in a mixture of 250 ml pyridine and 250 ml acetic anhydride. The mixture was then refluxed for half an hour. After cooling, the resulting crystals were filtered off and washed with acetic acid, ethanol and water. A solution of crude lup-20(29)-ene-3β,28-diyl diacetate (400 g) in chloroform was filtered through a column of alumina, and the column was washed with chloroform. The filtrate was then evaporated under reduced pressure. The residue was crystallized from chloroform/methanol to obtain 250 g of the title compound which according to TLC contained traces of lupeol acetate. After recrystallization from chloroform/methanol, the yield of pure compound was 239 g, mp. 222-223° C., $[α]_D$ +22° (c 0.4; CHCl$_3$). [Schulze H., Pieroh K.: Ber. Dtsch. Chem. Ges. 55, 2332 (1922)].

The $^1$H NMR spectrum of the title compound is as follows: 0.84 s, 0.84 s, 0.85 s, 0.97 s, 1.03 s, 1.68, 6×3H (6×CH$_3$); 2.04 s, 3H, 2.07 s, 3H (2×OAc); 2.44 ddd, 1H (J'=11.4, J''=10.9, J'''=0.7, H-19); 3.85 d, 1H (J=11.1, H-28a); 4.25 dd, 1H, (J'=11.1, J''=1.4, H-28b); 4.47 m, 1H (H-3α); 4.59 m, 1H (ΣJ=3.4, H-29E); 4.69 m, 1H (Σ=2.1, H-29Z).

Example 2

Lup-18-ene-3β,28-diyl diacetate

A solution of hydrogen bromide in acetic acid (38%, 1.4 l) was added to a solution of lup-20(29)-ene-3β,28-diyl diacetate (100 g, 190 mmol) in a mixture of benzene, acetic acid and acetic anhydride (1 1:0.5 1:50 ml). The reaction mixture was refluxed until the reaction was completed (TLC was developed in hexane/ether mixture). After cooling, the reaction mixture was poured into ice cold water (3:1) and extracted with benzene (3×0.5 l). The combined organic phases were washed with $NaHCO_3$ aqueous solution, $NaHSO_3$ solution and water and dried over magnesium sulphate. Usual working up procedure gave 90 g of dark brown residue. The dry powder was extracted in a Soxhlet extractor with acetone until it turned white. After drying in the air, the product was crystallized from butanone. The yield of the title compound was 74 g (74%), mp. 215-216° C., $[\alpha]_D$ +15° (c 0.45; $CHCl_3$). [Suokas E., Hase T.: Acta Chem. Scand., B 29, 139 (1975)].

The $^1H$ NMR spectrum of the title compound is as follows:
0.84 s, 0.85 s, 0.89 s, 0.90 s, 0.91 d, 3H (J=6.8), 0.99 d, 3H (J=6.8), 1.06 s, 7×3H (7×$CH_3$); 2.04 s, 3H, 2.05 s, 3H (2×OAc); 2.25 m, 2H (ΣJ~15); 2.43 m, 1H (ΣJ~15), 3.14 sept., 1H (J=7, H-20); 3.98 d, 1H (J=10.8, H-28a); 4.03 d, 1H (J=10.8, H-28b); 4.49 m, 1H (H-3α).

Example 3

21-oxo-lup-18-ene-3β,28-diyl diacetate

Lup-18-ene-3β,28-diyl diacetate (50 g; 95 mmol), sodium dichromate (22.5 g; 75.5 mmol) and sodium acetate (5 g) were dissolved in a mixture of benzene and acetic acid (0.7 l, 0.3 l). The reaction mixture was allowed to stand until the reaction was completed (TLC was developed in hexane/ether). After dilution with an excess of water, the mixture was extracted with benzene (3×300 ml). After usual working up procedure the title compound was obtained (45 g, 87%) as a pale-yellow crystalline foam which was used in the next step without further purification (see Example 4). Pure title compound has up. 205-206° C., $[\alpha]_D$ −35° (c 0.49; $CHCl_3$). Another way to the title compound is described in Sejbal J., Klinot J., Budešínský M., Protiva J.: Collect. Czech Chem. Commune 56, 2936 (1991).

The $^1H$ NMR spectrum of the title compound is as follows:
0.85 s, 0.86 s, 0.93 s, 0.94 s, 1.16 s, 1.17 d (J=7.1), 1.21 d (J=7.1), 7×3H (7×$CH_3$); 2.00 s, 3H, 2.05 s, 3H (2× OAc); 2.39 d, 1H (J=18.5, H-22); 2.87 dd, 1H (J'=11.9, J"=4.1, H-13β); 3.18 sept., 1H (J=6.6, H-20); 4.06 d, 1H (J=10.9, H-28a); 4.34 d, 1H (J=10.9, H-28b); 4.49 m, 1H (J~7, H-3α).

The following compounds were prepared by the above-mentioned procedure: (pivaloyloxy)methyl 3β,28-diacetoxy-18-oxo-19,20,21,29,30-pentanorlupan-22-oate acetoxymethyl 3β,28-diacetoxy-18-oxo-19,20,21,29,30-pentanorlupan-22-oate

Example 4

21,22-dioxolup-18-ene-3β,28-diyl diacetate

A solution of crude 21-oxo-lup-18-ene-3β,28-diyl diacetate (40 g; 74 mmol; containing about 85% of 21-oxo-lup-18-ene-3β,28-diyl diacetate) and selenium dioxide (160 g; 1.44 mol) in a mixture of dioxane (0.8 l) and acetic acid (0.4 l) was refluxed until the reaction was completed (TLC was developed in benzene/ether).

After cooling, the precipitated selenium was removed by filtration and the filtrate was slowly poured into a vigorously stirred excess of water. The red-orange precipitate was filtered off under reduced pressure, carefully washed with water and dried in the air. Dry crude 21,22-dioxo-lup-18-ene-3β,28-diyl diacetate was dissolved in chloroform and the solution was filtered through a column of alumina, the column was then washed with chloroform and the filtrate was evaporated under reduced pressure. The residue was crystallized from methyl acetate to give 28.9 g (82%) of the title compound as pale-orange needles, mp. 267-270° C., $[\alpha]_D$ −127° (c 0.32; $CHCl_3$). Another way to the title compound is described in Klinotová E., Cermáková J., Rejzek M., Krecek V., Sejbal J., Olšovský P., Klinot J.: Collect. Czech. Chem. Commun. 64, 329 (1999).

The $^1H$ NMR spectrum of the title compound is as follows:
0.85 s, 0.86 s, 0.94 s, 0.97 s, 1.18 s, 1.24 d (J=7.2), 1.26 d (J=7.2), 7×3H (7×$CH_3$); 1.93 s, 3H, 2.06 s, 3H (2×OAc); 3.12 dd, 1H (J'=12.5, J"'=3.8, H-13β); 3.36 sept., 1H (J=7.0, H-20); 4.02 d, 1H (J=11.1, H-28a); 4.49 dd, 1H (J'=10.2, J"=6.0, H-3α); 4.84 d, 1H (J=11.1, H-28b).

The following compounds were prepared by the above-mentioned procedure:

methyl 3β-acetoxy-21,22-dioxolup-18-en-28-oate acetoxymethyl 3β-acetoxy-21,22-dioxolup-18-en-28-oate (pivaloyloxy)methyl 3β-acetoxy-21,22-dioxolup-18-en-28-oate acetoxymethyl-3β,28-diacetoxy-18-oxo-19,20,21,29,30-pentanorlup-12-en-22-oate (pivaloyloxy)methyl 3β,28-diacetoxy-18-oxo-19,20,21,29,30-pentanorlup-12-en-22-oate 3β-hydroxy-30-oxolup-20(29)-en-28-oic acid [Dinda B., Hajra A. K., Das S. K., Chel G., Chakraborty R., Ranu B. C.: Indian. J. Chem., Sect. B 34, 624 (1995)].

acetoxymethyl 3β-hydroxy-30-oxolup-20(29)-en-28-oate (pivaloyloxy)methyl 3β-hydroxy-30-oxolup-20(29)-en-28-oate

Example 5

28-hydroxy-21-oxolup-18-en-3β-yl acetate

A solution of 21-oxolup-18-ene-3β,28-yl diacetate (20 g; 37 mmol) and potassium hydroxide (2.5 g; 45 mmol) in a mixture of benzene (200 ml) and ethanol (200 ml), was vigorously stirred until the reaction was completed (TLC was developed with the mixture hexane/ether).

The mixture was then poured into dilute (1:4) hydrochloric acid and extracted with benzene (3×200 ml). The organic layer was processed by the usual working up procedure to yield 17.5 g (95%) of a snow-white crystalline residue. Pure title compound has m.p. 292-294° C., $[\alpha]_D$ _69° (c 0.34; $CHCl_3$). [Klinotová E., Cermáková J., Rejzek M., Krecek V., Sejbal J., Olšovský P., Klinot J.: Collect Czech Chem. Commun. 64, 329 (1999)].

The $^1H$ NMR spectrum of the title compound is as follows:
0.85 s, 0.86 s, 0.93 s, 0.95 s, 1.13 s, 1.19 d (J=6.9), 1.21 d (J=6.9), 7×3H (7×$CH_3$); 1.92 d, 1H (J=18.6, H-22a); 2.05 s, 3H (OAc); 2.44 d, 1H (J=18.6, H-22b); 2.78 dd, 1H (J'=12.5, J"=3.4, H-13β); 3.19 sept., 1 H (J=6.9, H-20); 3.67 d, 1H (J=10.7, H-28a); 3.72 d, 1H (J=10.7, H-28b); 4.49 dd, 1H (J'=11.0, J"=5.5, H-3α).

Example 6

17β-methoxycarbonyl-28-norlup-20(29)-en-3β-yl[(2,2-dimethyl-1,3-dioxolan-4-yl)-methyl]carbonate A solution of methyl betulinate (0.5 g; 1.1 mmol) in a mixture of dichloromethane (8.0 ml), pyridine (0.4 ml) and chloroformate of solketal (0.8 ml; 4.1 mmol) was vigorously stirred for twelve hours at room temperature. After the reaction was complete the mixture was slowly poured into 100 ml of 5% hydrochloric acid and ice, twice extracted with chloroform. The combined organic layers were worked up in the usual manner and chromatographed on silica gel (10% ethyl acetate in hexane). After crystallization from methanol, the yield of pure compound was 0.45 g (67%), mp. 106-108° C., $[\alpha]_D$ +17° (c 0.56; $CHCl_3$).

The $^{13}C$ NMR spectrum of the title compound is as follows:

176.7, 155.1, 109.9, 109.6, 150.5, 85.8, 73.5, 73.4, 67.5, 66.4, 56.6, 55.4, 51.3, 50.4, 49.4, 47.0, 42.4, 40.7, 38.3, 38.2, 38.0, 37.1, 36.9, 34.2, 32.1, 30.6, 29.7, 27.8, 26.7, 25.5, 25.4, 22.6, 20.9, 19.3, 18.1, 16.4, 16.1, 15.9, 14.7.

The following compounds were prepared by the above-mentioned procedure:

17β-methoxycarbonyl-21-oxo-28-norlup-18-en-3β-yl[(2,2-dimethyl-1,3-dioxolan-4-yl)methyl]carbonate 17β-methoxycarbonyl-21,22-dioxo-28-norlup-18-en-3β-yl[(2,2-dimethyl-1,3-dioxolan-4-yl)methyl]carbonate 17β-carboxy-21-oxo-28-norlup-18-en-3β-yl[(2,2-dimethyl-1,3-dioxolan-4-yl)methyl]carbonate 17β-carboxy-28-norlup-20(29)-en-3β-yl[(2,2-dimethyl-1,3-dioxolan-4-yl)methyl]carbonate 17β-(acetoxymethylen)oxycarbonyl-28-norlup-20(29)-en-3β-yl[(2,2-dimethyl-1,3-dioxolan-4-yl)methyl]carbonate 17β-methylene-28-norlup-20(29)-en-3β-yl bis[(2,2-dimethyl-1,3-dioxolan-4-yl)methyl]dicarbonate

Example 7

17β-methoxycarbonyl-28-norlup-20(29)-en-3β-yl(2,3-dihydroxypropyl)carbonate

A solution of HCl (10%; 6.0 ml) was added to a solution of 17β-methoxycarbonyl-28-norlup-20(29)-en-3β-yl[(2,2-dimethyl-1,3-dioxolan-4-yl)methyl]carbonate (0.4 g; 0.6 mmol) in THF (8.0 ml) and the clear reaction mixture was stirred for five hours at 30° C. After the reaction was complete, the mixture was diluted with cold water (50 ml) and twice extracted with ethylacetate. The combined organic layers were worked up in the usual manner and chromatographed on silica gel (toluene/ethyl acetate, 5:1). The yield of white lyophilized (from acetic acid) powder was 0.28 g (76%), m p. 89-91° C., $[\alpha]_D$ +14° (c 0.58; $CHCl_3$).

The $^{13}C$ NMR spectrum of the title compound is as follows:

176.7, 155.6, 150.5, 109.6, 86.2, 70.1, 68.4, 63.2, 56.5, 55.4, 51.3, 50.4, 49.4, 47.0, 42.4, 40.7, 38.3, 38.2, 38.1, 37.1, 37.0, 34.2, 32.1, 30.6, 29.6, 27.9, 25.4, 23.6, 20.9, 19.3, 18.1, 16.4, 16.1, 15.9, 14.7.

The following compounds were prepared by the above-mentioned procedure:

17β-methoxycarbonyl-21-oxo-28-norlup-18-en-3β-yl(2,3-dihydroxypropyl)carbonate

17β-methoxycarbonyl-21,22-dioxo-28-norlup-18-en-3β-yl(2,3-dihydroxypropyl)carbonate 17β-carboxy-21-oxo-28-norlup-18-en-3β-yl(2,3-dihydroxypropyl)carbonate 17β-carboxy-28-norlup-20(29)-en-3β-yl(2,3-dihydroxypropyl)carbonate 17β-(acetoxymethylen)oxycarbonyl-28-norlup-20(29)-en-3β-yl(2,3-dihydroxypropyl)carbonate 17β-methylene-28-norlup-20(29)-en-3β-yl bis(2,3-dihydroxypropyl)dicarbonate

Example 8

3β-acetoxy-lup-20(29)-en-28-oyl fluoride

Diethylaminosulphur trifluoride (0.2 ml; 1.3 mmol) was added dropwise to a solution of acetylbetulinic acid (0.2 g; 0.4 mmol) in dry chloroform (2 ml) and the reaction mixture was stirred for one hour at room temperature. After the reaction was complete, the mixture was slowly poured into cold water (50 ml) and twice extracted with chloroform. The combined organic fractions were worked up in the usual manner and chromatographed on silica gel (3% ethyl acetate in hexane). The residue was crystallized from isopropyl alcohol to obtain 0.13 g (65%) of the title compound as small white crystals, m.p. 211-214° C. (decomp.), $[\alpha]_D$ +38° (c 0.44; $CHCl_3$).

The $^{13}C$ NMR spectrum of the title compound is as follows:

171.0 s, 165.2 d (J=375), 149.3 s, 110.4 s, 80.9 s, 57.0 d (J=39), 55.4 s, 50.4 s, 49.1 s, 46.7 s, 42.4 s, 40.7 s, 38.5 s, 38.4 s, 37.8 s, 37.1 s, 35.6 s, 34.2 s, 30.9 s, 30.0 s, 29.7 s, 27.9 s, 25.3 s, 23.7 s, 21.3 s, 20.8 s, 19.3 s, 18.1 s, 16.5 s, 16.2 s, 15.9 s, 14.7 s.

The following compounds were prepared by the above-mentioned procedure:

3β-acetoxy-21-oxolup-18-en-28-oyl fluoride

3β-acetoxylup-28-oyl fluoride 3-oxolup-20(29)-en-28-oyl fluoride

3β-acetoxy-30-oxolup-20(29)-en-28-oyl fluoride

Example: 9

Biological Activity of Betulinines

In Vitro Cytotoxic Activity of Betulinines on Tumor Cell Lines

One of the parameters used as the basis for colorimetric assays is the metabolic activity of viable cells. For example, a microtiter assay which uses the tetrazolium salt MTT is now widely used to quantitate cell proliferation and cytotoxicity [Hajdúch M, Mihál V, Minarík J, Fáber E, Šafářová M, Weigl E, Antálek P.: Cytotechnology, 1996, 19, 243-245]. For instance, this assay is used in drug screening programs and in chemosensitivity testing. Because tetrazolium salts are cleaved only by metabolically active cells, these assays exclusively detect viable cells. In the case of the MTT assay, yellow soluble tetrazolium salt is reduced to a coloured water-insoluble formazan salt. After it is solubilized, the formazan formed can easily and rapidly be quantified in a conventional ELISA plate reader at 570 nm (maximum absorbency). The quantity of reduced formazan corresponds to the number of vital cells in the culture.

Human T-lymphoblastic leukaemia cell line CEM was used for routine screening of these compounds. To prove a common mechanism of action, selected compounds which showed activity in a screening assay were tested in a panel of cell lines (Table 2). These lines were from different species and of different histogenetic origin and they possess various alterations in cell cycle regulatory proteins and hormone dependence status (Table 2). The cells were maintained in Nunc/Corning 80 cm² plastic tissue culture flasks and cultured in cell culture medium (DMEM with 5 g/l glucose, 2 mM glutamine, 100 U/ml penicillin, 100 µg/ml streptomycin, 10% foetal calf serum and sodium bicarbonate). Individual compounds were dissolved in 10% dimethylsulfoxide/saline, pH 8.0.

The cell suspensions that were prepared and diluted according to the particular cell type and the expected target cell density (2.500-30.000 cells per well based on cell growth characteristics) were added by pipette (80 µl) into 96/well microtiter plates. Inoculates were allowed a pre-incubation period of 24 hours at 37° C. and 5% $CO_2$ for stabilisation. Four-fold dilutions of the intended test concentration were added at time zero in 20 µl aliquots to the microtiter plate wells. Usually, test compounds were evaluated at six 4-fold dilutions. In routine testing, the highest well concentration was 250 µM, but it may differ, depending on the agent. All drug concentrations were examined in duplicate. Incubations of cells with the test compounds lasted for 72 hours at 37° C., in 5% $CO_2$ atmosphere and 100% humidity. At the end of the incubation period, the cells were assayed by using the MTT assay. Ten microliters of the MTT stock solution were pipetted into each well and incubated further for 1-4 hours. After this incubation period, formazan was solubilized by the addition of 100 µl/well of 10% SDS in water (pH=5.5) followed by further incubation at 37° C. overnight. The optical density (OD) was measured at 540 nm with the Labsystem iEMS Reader MF(UK). The tumour cell survival (TCS) was calculated using the following equitation: TCS= $(OD_{drug\ exposed\ well}/\text{mean }OD_{control\ wells}) \times 100\%$. The $TCS_{50}$ value, the drug concentration lethal to 50% of the tumour cells, was calculated from the obtained dose response curves.

To evaluate the anti-cancer activity of betulinines, their cytotoxic activity against CEM cell line was examined using the screening assay. Potent compounds were further tested against a panel of cell lines of different histogenetic and species origin (Table 2).

TABLE 2

Cytotoxic activity of selected betulinines against a panel of different (non)malignant cell lines.

| Cell Line | Description | Compound ($TCS_{50}[\mu M]$) | | | | | | | | |
|---|---|---|---|---|---|---|---|---|---|---|
| | | Betulinic acid | II.4 | II.7 | II.14 | II.26 | II.37 | II.45 | II.52 | II.55 |
| B16 | mouse melanoma | 36 | 35 | | 9.3 | | | | | |
| B16F | mouse melanoma, metastatic | 4.6 | 68 | | 12 | | | | | |
| SW620 | human colon cancer, metastasis | 250 | 5.9 | | 5.9 | | | | | |
| U87MG | human glioblastoma | 250 | 24 | | 8.4 | | | | | |
| HepG2 | human hepatocellular carcinoma | 3.6 | 5.1 | | 7.1 | | | | | |
| A549 | human lung adenocarcinoma | 236 | 6.7 | | 3.3 | | | | | |
| MCF-7 | human breast cancer, estrogen dependent, p53+/+, Rb +/+ | 194 | 13 | | 4.3 | | | | | |
| U2OS | human osteosarcoma, p53+/−, Rb +/− | 250 | 4.3 | | 3.9 | | | | | |
| Saos2 | human rhabdomyosarcoma, p53−/−, Rb−/− | 250 | 7.9 | | 4.8 | | | | | |
| BT549 | human breast cancer, p53mut/mut | 250 | 15 | | 6.3 | | | | | |
| MDA-MB-238 | human breast cancer, estrogen independent, p53mut/mut | 195 | 3.3 | | 2.4 | | | | | |
| LNCaP | human prostate cancer, androgen dependent | 244 | 3.3 | | 3.6 | | | | | |
| DU145 | human prostate cancer, androgen independent, Rb−/− | 241 | 2.0 | | 2.8 | | | | | |
| HT-29 | human colon cancer | 250 | 5.6 | | 4.7 | | | | | |
| OVCAR-3 | human ovarian cancer | 164 | 4.7 | | 2.6 | | | | | |
| Caco-2 | human colon cancer | 20 | 8.1 | | 7.7 | | | | | |
| MEL-3 | human melanoma | 2.7 | 5.9 | | 3.7 | | | | | |
| Lymphocytes | human normal lymphocytes | 250 | 85 | | 25 | | | | | |
| NIH3T3 | mouse immortalised fibroblasts | 250 | 97 | | 16 | | | | | |
| K562-CdA | human promyelocytic leukemia, cladrubin resistant | 250 | 5.2 | | 2.1 | | | | | |
| K562-GEM | human promyelocytic leukemia, gemcitabin resistant | 101 | 5.0 | | 2.4 | | | | | |

TABLE 2-continued

Cytotoxic activity of selected betulinines against a panel of different (non)malignant cell lines.

| Cell Line | Description | Compound (TCS$_{50}$[μM]) | | | | | | | | |
|---|---|---|---|---|---|---|---|---|---|---|
| | | Betulinic acid | II.4 | II.7 | II.14 | II.26 | II.37 | II.45 | II.52 | II.55 |
| K562-ARA-C | human promyelocytic leukemia, cytarabin resistant | 250 | 6.4 | | 1.6 | | | | | |
| K562-FLUD | human promyelocytic leukemia, fludarabin resistant | 250 | 4.9 | | 1.3 | | | | | |
| CEM | human T-lymphoblastic leukemia | 250 | 7.2 | 6.3 | 3.0 | 1.1 | 28 | 13 | 8 | 19 |
| CEM-DNR 1/C2 | human T-lymphoblastic leukemia, daunorubicin resistant | 250 | 10 | | 1.6 | | | | | |
| CEM-DNR bulk | human T-lymphoblastic leukemia, daunorubicin resistant | 250 | 5.2 | | 3.3 | | | | | |
| CEM-VCR 1/F3 | human T-lymphoblastic leukemia, vincristin resistant | 19 | 38 | | 5.9 | | | | | |
| CEM-VCR 3/D5 | human T-lymphoblastic leukemia, vincristin resistant | 24 | 13 | | 7.8 | | | | | |
| CEM-VCR bulk | human T-lymphoblastic leukemia, vincristin resistant | 69 | 28 | | 7.0 | | | | | |

In contrast to betulinic acid, which is reported to be an agent selective for neuroectodermal derived tumours, there was no significant difference in sensitivity of betulinines to tumours of different histogenetic origin.

The compounds are effective in submicromolar or low micromolar concentrations. However, the non-malignant cells, e.g. NIH3T3 fibroblasts and normal human lymphocytes, tolerated substantially higher doses of betulinines than the tumour cells suggesting a favourable therapeutic index.

Notably, the effectiveness of betulinines was found to be identical in cell lines bearing various mutations or deletions in cell cycle associated proteins (Table 2). This indicates that these substances should be equally effective in tumours with various alterations of tumour suppresser genes, namely p53, Rb, etc.

Furthermore, betulinines were shown to be equally effective in drug resistant cell lines as on their maternal counterparts, thereby suggesting that classical mechanisms of multidrug resistance apparently do not apply to these compounds. This particular characteristic should be of significant therapeutic benefit to chemotherapy resistant cancer patients.

Finally, the cytotoxic activity of betulinines is independent of the hormonal status of cancer cells, so the compounds should be equally effective in treatment of hormone dependent and independent cancers.

Those skilled in the art will recognise, or be able to ascertain using no more than routine experimentation, many equivalents to the specific embodiments of the invention described herein. Such equivalents are intended to be encompassed by the claims.

The invention claimed is:
1. A compound of structural formula Ia, or a pharmaceutically acceptable salt thereof,

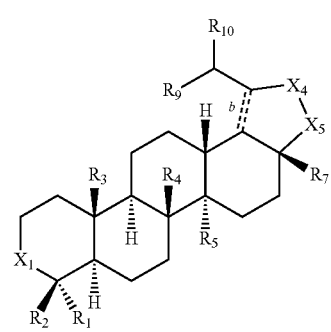

Ia selected from the following:

| No. | X$^1$ | X$^4$ | X$^5$ | b | R$^{1-5}$ |
|---|---|---|---|---|---|
| II.1 | CHOAc | C=O | CH$_2$ | double | Me |
| II.4 | CHOAc | C=O | C=O | double | Me |
| II.5 | CHOCOCH$_2$Cl | C=O | CH$_2$ | double | Me |
| II.6 | CHOCOCH$_2$Cl | C=O | C=O | double | Me |
| II.7 | CHOH | C=O | C=O | double | Me |
| II.8 | CHOH | C=O | C=O | double | Me |
| II.9 | CHOAc | C=O | CH$_2$ | double | Me |
| II.11 | CHOAc | C=O | C=O | double | Me |

-continued

| No. | X$^1$ | X$^4$ | X$^5$ | b | R$^{1-5}$ |
|---|---|---|---|---|---|
| II.12 | CHOAc | CH$_2$ | CH$_2$ | single | Me |
| II.13 | CHOAc | CH$_2$ | CH$_2$ | single | Me |
| II.15 | CHOAc | CH$_2$ | CH$_2$ | single | Me |
| II.16 | CHOAc | C=O | CHOAc | double | Me |
| II.17 | C=O | CH$_2$ | CH$_2$ | single | Me, (R$^2$:H) |
| II.18 | CHOAc | CH$_2$ | CH$_2$ | single | Me |
| II.19 | CHOH | CH$_2$ | CH$_2$ | single | Me |
| II.20 | CHOH | CH$_2$ | CH$_2$ | single | Me |
| II.21 | CHOH | CH$_2$ | CH$_2$ | single | Me |
| II.22 | CHOH | CH$_2$ | CH$_2$ | single | Me |
| II.23 | CHOAc | C=O | C=O | double | Me |
| II.24 | CHOH | CH$_2$ | CH$_2$ | single | Me |
| II.25 | CHOH | CH$_2$ | CH$_2$ | single | Me |
| II.26 | CHOH | C=O | C=O | double | Me |
| II.27 | CHOH | C=O | CH$_2$ | double | Me |
| II.30 | CHOH | C=O | CH$_2$ | double | Me |
| II.31 | CHOH | C=O | CH$_2$ | double | Me |
| II.32 | CHOH | C=O | CH$_2$ | double | Me |
| II.35 | B | C=O | CH$_2$ | double | Me |
| II.36 | CHOAc | C=O | C=O | double | Me |
| II.37 | CHOH | C=O | C=O | double | Me |
| II.38 | CHOH | C=O | C=O | double | Me |
| II.40 | B | C=O | C=O | double | Me |
| II.42 | B | C=O | CH$_2$ | double | Me |
| II.44 | B | CH$_2$ | CH$_2$ | single | Me |
| II.46 | B | CH$_2$ | CH$_2$ | single | Me |
| II.48 | B | CH$_2$ | CH$_2$ | single | Me |
| II.49 | CHOAc | CH$_2$ | CH$_2$ | single | Me |
| II.51 | B | CH$_2$ | CH$_2$ | single | Me |
| II.52 | CHOAc | CH$_2$ | CH$_2$ | single | Me |
| II.53 | CHOAc | CH$_2$ | CH$_2$ | single | Me |
| II.54 | CHOAc | C=O | CH$_2$ | double | Me |
| II.55 | CHOAc | CH$_2$ | CH$_2$ | single | Me |
| II.56 | CHOAc | CH$_2$ | CH$_2$ | single | Me |
| II.57 | C=O | CH$_2$ | CH$_2$ | single | Me |
| II.58 | CHOAc | CH$_2$ | CH$_2$ | single | Me |

| No. | R$^7$ | R$^9$ | R$^{10}$ |
|---|---|---|---|
| II.1 | COOH | Me | Me |
| II.4 | COOMe | Me | Me |
| II.5 | CH$_2$OAc | Me | Me |
| II.6 | CH$_2$OAc | Me | Me |
| II.7 | CH$_2$OAc | Me | Me |
| II.8 | CH$_2$OH | Me | Me |
| II.9 | COOCH$_2$O—COBu$^t$ | Me | Me |
| II.11 | COOCH$_2$OCOBu$^t$ | Me | Me |
| II.12 | COOH | CH$_2$ | CN |
| II.13 | COOH | CH$_2$ | COOH |
| II.15 | COOH | CH$_2$ | CH$_2$OH |
| II.16 | CH$_2$OAc | Me | Me |
| II.17 | CH$_2$OAc | Me | Me |
| II.18 | COOH | CH$_2$ | COH |
| II.19 | COOH | (20-R)—OH | Me |
| II.20 | COOH | (20-S)—OH | Me |
| II.21 | COOH | (20-R)—CH$_2$OH | Me |
| II.22 | COOH | (20-S)—CH$_2$OH | Me |
| II.23 | COOCH$_2$OCOMe | Me | Me |
| II.24 | COOCH$_2$OCOBu$^t$ | CH$_2$ | COH |
| II.25 | COOCH$_2$OCOMe | CH$_2$ | COH |
| II.26 | COOMe | Me | Me |
| II.27 | COOCH$_2$OCOBu$^t$ | Me | Me |
| II.30 | CH$_2$OAc | Me | Me |
| II.31 | COOMe | Me | Me |
| II.32 | COOCH$_2$OCOMe | Me | Me |
| II.35 | COOMe | Me | Me |
| II.36 | CH$_2$OH | Me | Me |
| II.37 | COOCH$_2$OCOMe | Me | Me |
| II.38 | COOCH$_2$OCOBu$^t$ | Me | Me |
| II.40 | COOMe | Me | Me |
| II.42 | COOH | Me | Me |
| II.44 | COOH | CH$_2$ | Me |
| II.46 | COOMe | CH$_2$ | Me |
| II.48 | COOCH$_2$OCOMe | CH$_2$ | Me |
| II.49 | CH$_2$OTs | CH$_2$ | Me |
| II.51 | HB | CH$_2$ | Me |
| II.52 | COOCOMe | CH$_2$ | COH |
| II.53 | COOCOMe | CH$_2$ | Me |
| II.54 | COF | Me | Me |
| II.55 | COF | CH$_2$ | Me |
| II.56 | COF | CH$_2$ | COH |
| II.57 | COF | CH$_2$ | Me |
| II.58 | COF | Me | Me | where:
B is CHOC(O)OCH$_2$-2,2-dimethyl-1,3-dioxolan-4-yl
Ts is OSO$_2$C$_6$H$_4$CH$_3$.

2. The compound of claim 1 wherein X$^1$ is CHOAc, X$^4$ and X$^5$ are each CO, b is a double bond, R$^{1-5}$ are methyl, R$^7$ is COOMe, R$^9$ is Me and R$^{10}$ is Me.

3. A pharmaceutical composition comprising a compound of structural formula Ia, or a pharmaceutically acceptable salt thereof,

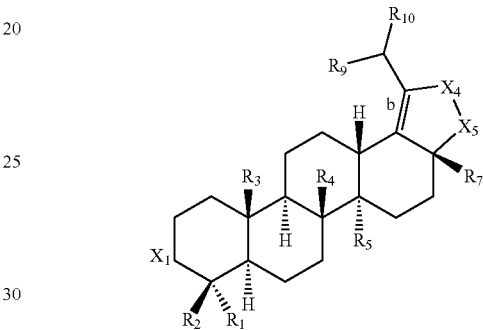

Ia selected from the group consisting of:

| No. | X$^1$ | X$^4$ | X$^5$ | b | R$^{1-5}$ |
|---|---|---|---|---|---|
| II.1 | CHOAc | C=O | CH$_2$ | double | Me |
| II.4 | CHOAc | C=O | C=O | double | Me |
| II.5 | CHOCOCH$_2$Cl | C=O | CH$_2$ | double | Me |
| II.6 | CHOCOCH$_2$Cl | C=O | C=O | double | Me |
| II.7 | CHOH | C=O | C=O | double | Me |
| II.8 | CHOH | C=O | C=O | double | Me |
| II.9 | CHOAc | C=O | CH$_2$ | double | Me |
| II.11 | CHOAc | C=O | C=O | double | Me |
| II.12 | CHOAc | CH$_2$ | CH$_2$ | single | Me |
| II.13 | CHOAc | CH$_2$ | CH$_2$ | single | Me |
| II.15 | CHOAc | CH$_2$ | CH$_2$ | single | Me |
| II.16 | CHOAc | C=O | CHOAc | double | Me |
| II.17 | C=O | CH$_2$ | CH$_2$ | single | Me, (R$^2$:H) |
| II.18 | CHOAc | CH$_2$ | CH$_2$ | single | Me |
| II.19 | CHOH | CH$_2$ | CH$_2$ | single | Me |
| II.20 | CHOH | CH$_2$ | CH$_2$ | single | Me |
| II.21 | CHOH | CH$_2$ | CH$_2$ | single | Me |
| II.22 | CHOH | CH$_2$ | CH$_2$ | single | Me |
| II.23 | CHOAc | C=O | C=O | double | Me |
| II.24 | CHOH | CH$_2$ | CH$_2$ | single | Me |
| II.25 | CHOH | CH$_2$ | CH$_2$ | single | Me |
| II.26 | CHOH | C=O | C=O | double | Me |
| II.27 | CHOH | C=O | CH$_2$ | double | Me |
| II.30 | CHOH | C=O | CH$_2$ | double | Me |
| II.31 | CHOH | C=O | CH$_2$ | double | Me |
| II.32 | CHOH | C=O | CH$_2$ | double | Me |
| II.35 | B | C=O | CH$_2$ | double | Me |
| II.36 | CHOAc | C=O | C=O | double | Me |
| II.37 | CHOH | C=O | C=O | double | Me |
| II.38 | CHOH | C=O | C=O | double | Me |
| II.40 | B | C=O | C=O | double | Me |
| II.42 | B | C=O | CH$_2$ | double | Me |
| II.44 | B | CH$_2$ | CH$_2$ | single | Me |
| II.46 | B | CH$_2$ | CH$_2$ | single | Me |
| II.48 | B | CH$_2$ | CH$_2$ | single | Me |

-continued

| No. | | | | | |
|---|---|---|---|---|---|
| II.49 | CHOAc | CH$_2$ | CH$_2$ | single | Me |
| II.51 | B | CH$_2$ | CH$_2$ | single | Me |
| II.52 | CHOAc | CH$_2$ | CH$_2$ | single | Me |
| II.53 | CHOAc | CH$_2$ | CH$_2$ | single | Me |
| II.54 | CHOAc | C=O | CH$_2$ | double | Me |
| II.55 | CHOAc | CH$_2$ | CH$_2$ | single | Me |
| II.56 | CHOAc | CH$_2$ | CH$_2$ | single | Me |
| II.57 | C=O | CH$_2$ | CH$_2$ | single | Me |
| II.58 | CHOAc | CH$_2$ | CH$_2$ | single | Me |

| No. | R$^7$ | R$^9$ | R$^{10}$ |
|---|---|---|---|
| II.1 | COOH | Me | Me |
| II.4 | COOMe | Me | Me |
| II.5 | CH$_2$OAc | Me | Me |
| II.6 | CH$_2$OAc | Me | Me |
| II.7 | CH$_2$OAc | Me | Me |
| II.8 | CH$_2$OH | Me | Me |
| II.9 | COOCH$_2$OCOBu$^t$ | Me | Me |
| II.11 | COOCH$_2$OCOBu$^t$ | Me | Me |
| II.12 | COOH | CH$_2$ | CN |
| II.13 | COOH | CH$_2$ | COOH |
| II.15 | COOH | CH$_2$ | CH$_2$OH |
| II.16 | CH$_2$OAc | Me | Me |
| II.17 | CH$_2$OAc | Me | Me |
| II.18 | COOH | CH$_2$ | COH |
| II.19 | COOH | (20-R)—OH | Me |
| II.20 | COOH | (20-S)—OH | Me |
| II.21 | COOH | (20-R)—CH$_2$OH | Me |
| II.22 | COOH | (20-S)—CH$_2$OH | Me |
| II.23 | COOCH$_2$OCOMe | Me | Me |
| II.24 | COOCH$_2$OCOBu$^t$ | CH$_2$ | COH |
| II.25 | COOCH$_2$OCOMe | CH$_2$ | COH |
| II.26 | COOMe | Me | Me |
| II.27 | COOCH$_2$OCOBu$^t$ | Me | Me |
| II.30 | CH$_2$OAc | Me | Me |
| II.31 | COOMe | Me | Me |
| II.32 | COOCH$_2$OCOMe | Me | Me |
| II.35 | COOMe | Me | Me |
| II.36 | CH$_2$OH | Me | Me |
| II.37 | COOCH$_2$OCOMe | Me | Me |
| II.38 | COOCH$_2$OCOBu$^t$ | Me | Me |
| II.40 | COOMe | Me | Me |
| II.42 | COOH | Me | Me |
| II.44 | COOH | CH$_2$ | Me |
| II.46 | COOMe | CH$_2$ | Me |
| II.48 | COOCH$_2$OCOMe | CH$_2$ | Me |
| II.49 | CH$_2$OTs | CH$_2$ | Me |
| II.51 | HB | CH$_2$ | Me |
| II.52 | COOCOMe | CH$_2$ | COH |
| II.53 | COOCOMe | CH$_2$ | Me |
| II.54 | COF | Me | Me |
| II.55 | COF | CH$_2$ | Me |
| II.56 | COF | CH$_2$ | COH |
| II.57 | COF | CH$_2$ | Me |
| II.58 | COF | Me | Me | wherein:
B is CHOC(O)OCH$_2$-2,2-dimethyl-1,3-dioxolan-4-yl
Ts is OSO$_2$C$_6$H$_4$CH$_3$.

and a pharmaceutically acceptable diluent, excipient or carrier.

4. The pharmaceutical composition of claim 3, wherein X$^1$ is CHOAc, X$^4$ and X$^5$ are each C=O, b is a double bond, R$^{1-5}$ are Me, R$^7$ is COOMe, R$^9$ is Me and R$^{10}$ is Me.

* * * * *